(12) United States Patent
Reichle et al.

(10) Patent No.: US 11,185,364 B2
(45) Date of Patent: Nov. 30, 2021

(54) HF SURGICAL INSTRUMENT

(71) Applicant: Aesculap AG, Tuttlingen (DE)

(72) Inventors: Heiko Reichle, Tuttlingen (DE); Dirk Faitsch, Korb (DE); Patrick Heizmann, Hüfingen (DE); Nikolaus Hafner, Tuttlingen (DE); Thomas Maser, Zimmern ob Rottweil (DE)

(73) Assignee: AESCULAP AG, Tuttlingen (DE)

( * ) Notice: Subject to any disclaimer, the term of this patent is extended or adjusted under 35 U.S.C. 154(b) by 314 days.

(21) Appl. No.: 15/023,830

(22) PCT Filed: Sep. 22, 2014

(86) PCT No.: PCT/EP2014/070132
§ 371 (c)(1),
(2) Date: Mar. 22, 2016

(87) PCT Pub. No.: WO2015/044086
PCT Pub. Date: Apr. 2, 2015

(65) Prior Publication Data
US 2016/0235472 A1 Aug. 18, 2016

(30) Foreign Application Priority Data
Sep. 25, 2013 (DE) ...................... 10 2013 110 595.5

(51) Int. Cl.
*A61B 18/14* (2006.01)
*A61B 18/00* (2006.01)
*A61B 18/12* (2006.01)

(52) U.S. Cl.
CPC ........ *A61B 18/1445* (2013.01); *A61B 18/148* (2013.01); *A61B 18/1206* (2013.01);
(Continued)

(58) Field of Classification Search
CPC ........... A61B 2018/00172; A61B 2018/00178; A61B 2018/126; A61B 2018/145;
(Continued)

(56) References Cited

U.S. PATENT DOCUMENTS 5,269,780 A * 12/1993 Roos .................. A61B 18/1442
606/42
5,527,313 A * 6/1996 Scott .................. A61B 17/2909
606/41
(Continued)

FOREIGN PATENT DOCUMENTS

DE 2455171 8/1976
DE 19730724 1/1998
(Continued)

OTHER PUBLICATIONS

German Search Report dated Mar. 25, 2014 for German Application No. 10 2013 110 595.5 with translation.
(Continued)

*Primary Examiner* — Ronald Hupczey, Jr.
*Assistant Examiner* — Bradford C. Blaise

(57) ABSTRACT

An HF surgical instrument includes two instrument branches movable toward each other into a closing position. Each branch is equipped with at least one electrode and can be supplied with electric power from a power source. The HF instrument includes a separately configured bridge which is connectable to the power source via at least one electric connection or at least one electric line and includes at least one electrically conductive contact point for supplying the at least one electrode with electric power. The bridge can be introduced to at least one of the two branches so that the at least one contact point is electrically contacted by the at least
(Continued)

Figure 1:
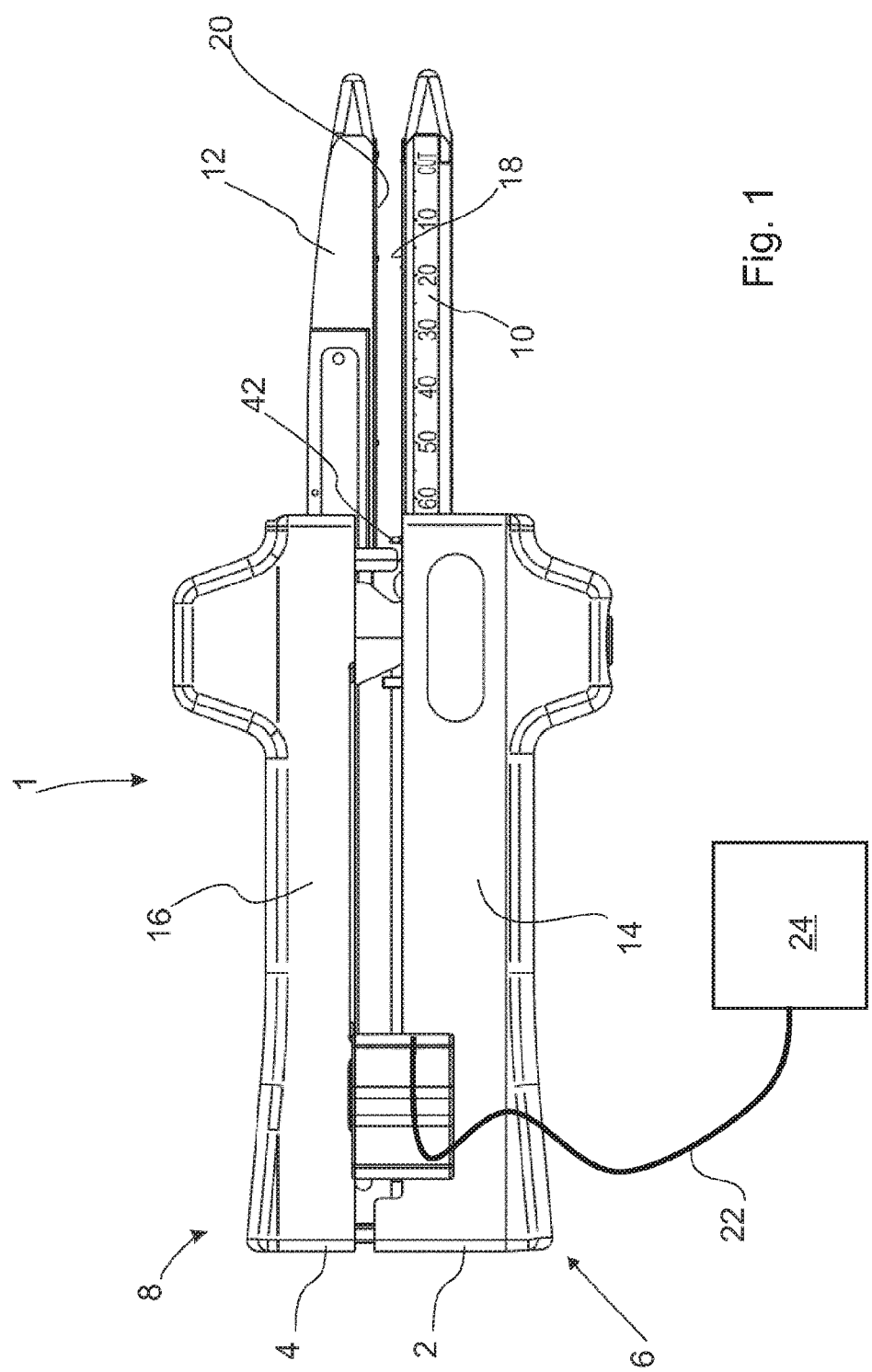

one electrode. A method of assembling a HF surgical instrument includes equipping two instrument branches with at least one electrode.

15 Claims, 3 Drawing Sheets

(52) U.S. Cl.
CPC ............... *A61B 2018/0063* (2013.01); *A61B 2018/00178* (2013.01); *A61B 2018/126* (2013.01); *A61B 2018/145* (2013.01); *A61B 2018/1467* (2013.01); *A61B 2018/1495* (2013.01)

(58) Field of Classification Search
CPC .... A61B 2018/1452; A61B 2018/1455; A61B 2018/1457; A61B 2018/146; A61B 2018/1462; A61B 2018/1467; A61B 2018/1495; A61B 18/12; A61B 18/1206; A61B 18/14; A61B 18/1402; A61B 18/1442; A61B 18/1445; A61B 18/1447
See application file for complete search history.

(56) References Cited

U.S. PATENT DOCUMENTS

| | | | |
|---|---|---|---|
| 5,951,549 | A | 9/1999 | Richardson et al. |
| 5,976,132 | A * | 11/1999 | Morris ............... A61B 18/1445 |
| | | | 128/DIG. 22 |
| 8,251,989 | B1 | 8/2012 | Newton |
| 2003/0199869 | A1* | 10/2003 | Johnson ............. A61B 18/1445 |
| | | | 606/50 |
| 2004/0153020 | A1 | 8/2004 | Bartel |
| 2007/0260241 | A1* | 11/2007 | Dalla Betta ........ A61B 18/1442 |
| | | | 606/48 |
| 2008/0033428 | A1* | 2/2008 | Artale ................ A61B 18/1442 |
| | | | 606/51 |
| 2008/0215048 | A1* | 9/2008 | Hafner ............... A61B 17/2841 |
| | | | 606/42 |
| 2010/0292690 | A1 | 11/2010 | Livneh |
| 2011/0178515 | A1 | 7/2011 | Bloom |
| 2012/0080477 | A1* | 4/2012 | Leimbach ........ A61B 17/07207 |
| | | | 227/175.2 |
| 2013/0046337 | A1* | 2/2013 | Evans .................... A61B 17/29 |
| | | | 606/205 |
| 2013/0296843 | A1* | 11/2013 | Boudreaux ............ A61B 18/18 |
| | | | 606/33 |
| 2016/0235472 | A1 | 8/2016 | Reichle et al. |

FOREIGN PATENT DOCUMENTS

| | | |
|---|---|---|
| DE | 10205093 | 1/2003 |
| DE | 10323533 | 12/2004 |
| DE | 102011001372 | 9/2012 |
| JP | H06162860 A | 6/1994 |
| JP | H10258063 A | 9/1998 |
| JP | 2016531611 A | 10/2016 |

OTHER PUBLICATIONS

International Search Report in related International Application No. PCT/EP2014/070132, dated Dec. 1, 2014.
Written Opinion issued in related International Application No. PCT/ep2014/070132, dated Dec. 1, 2014.
Notification of Reasons for Rejection for Japanese Application No. 2016-516981, dated Jun. 26, 2018, with translation, 13 pages.
Chinese Office Action for Chinese Application No. 201480056679.4, dated Aug. 29, 2018 with translation, 16 pages.
Japanese Office Action received in Application No. 2019-148938 dated Oct. 2, 2020, 8 pages.

* cited by examiner

HF SURGICAL INSTRUMENT

RELATED APPLICATIONS

This application is the U.S. National Phase entry of International Application No. PCT/EP2014/070132, filed Sep. 22, 2014, which is related to and claims the benefit of priority of German Application No. 10 2013 110 595.5, filed Sep. 25, 2013. The contents of International Application No. PCT/EP2014/070132 and German Application No. 10 2013 110 595.5 are incorporated by reference herein in their entireties for all purposes.

FIELD

The present invention relates generally to a HF surgical instrument, and more particularly to a bipolar HF sealing instrument and a method of assembling said HF surgical instrument.

BACKGROUND

It is known that such surgical HF instrument substantially consists of at least one instrument branch in which at least one electrode is contained and, respectively, on which at least one electrode is arranged and of an electric line through which electric power can be supplied to the HF instrument and especially to the electrode thereof from an external electric power source. An external power source may be, for example, a high-frequency AC power source in the form of an HF generator.

It is further known that such surgical HF instrument, in particular a bipolar-type HF sealing instrument, can be used for causing thermally induced modification or destruction of tissue cells. It is frequently the aim of such tissue impact using a high-frequency AC (HF) to cause hemostasis, tissue division or tissue sealing on a human or animal body. For example, vessels and tissue structures can be permanently and safely thermo-fused by the HF sealing instrument. Thermo-fusion is carried out, on the one hand, by applying power via two opposed instrument branches equipped with electrodes between which the tissue to be treated is clamped and, on the other hand, by pressure by which the tissue to be treated is compressed between the instrument branches.

In order to reliably supply the at least one electrode of said HF surgical instrument with electric power it is necessary that the energy-supplying electric line and the electrode of the handle unit are reliably electrically interconnected. In practice, high quality demands are made on the electric connections between the electrodes and the electric line inside such HF surgical instrument. First of all, the electric connections are to be designed to be preferably low-impedance for as low-loss energy transmission as possible. In order to obtain reliable function of the HF surgical instrument the electric connections inside said instrument moreover are to be made contact-safe. Furthermore, the tissue-contacting electrode sides are to be made bio-compatible and, respectively, are to remain bio-compatible also after assembly of the HF instrument. Further, such HF surgical instrument shall be adapted to be assembled and provided in a most cost-effective manner. Especially with a bipolar design of the HF surgical instrument also the mobility of the tool elements is not to be limited. Finally, the electric conduction for supplying the HF surgical instrument with electric power preferably is to be carried out via one tool element only.

Frequently, said HF surgical instruments are manufactured and used also as single-use instruments, as they are called. In particular with such design variant of a HF surgical instrument, it may moreover be desirable to minimize the assembling expenditure for providing the instrument so as to achieve comparatively low provision costs.

HF surgical instruments in which the electric connections are fabricated or manufactured by soldered connections, i.e. by cohesive connection, are known from the state of the art. Although this type of electric connection between the electric line and the electrode meets the afore-mentioned quality demands as regards reliability, transmission losses and most largely contact safety, the soldered connections in this context turn out to be a drawback, however, especially when the electrode or electrodes, resp., are provided in segmented arrangement and, respectively, segmentally in or on the handle unit of the HF surgical instrument, which have to be individually energized. In most cases the electric line is a multi-core line so that plural cores of said line have to be soldered to each individual segment of the segmental electrode. That is to say, the more individual electrode segments are provided in and, resp., on the handle unit, the more frequently the soldering process has to be repeated for connecting the electric line to the individual electrodes. With an increasing number of individual electrode segments it becomes increasingly difficult in the case of restricted space conditions within the HF surgical instrument, however, to guide the individual cores of the electric line through the HF surgical instrument to the individual electrode bodies. Therefore, said soldered connections require certain expenditure of time for fabricating and, resp., assembling a HF surgical instrument, which renders the manufacturing costs of a HF surgical instrument fabricated in this way comparatively high.

Furthermore, a HF surgical instrument is frequently intended to be fabricated and, resp., assembled in a clean room. In such clean room soldering is possible only to a limited extent, usually while observing strict requirements regarding working and/or process safety. It is also linked with a financial effort to observe said strict requirements, which causes the manufacturing costs of the instrument to be comparatively high.

Moreover, the inserted electrodes may have a comparatively high thermal capacity so that fusing the material and thus providing the soldered connection requires comparatively high expenditure of time.

The use of soldered connections as electric connection between the electric line and the at least one electrode of the handle unit may also turn out to be a drawback, when the electrode is to be manufactured of a material which is suited for soldering only to a limited extent, not directly or not at all. Thus the use of soldered connections subjects the provision and assembly of HF surgical instruments to several restrictions.

SUMMARY

It is the object of the invention to reduce the assembling effort for a HF surgical instrument using as simple means as possible in terms of construction. It is one objective to reduce the costs for assembly and, respectively, provision of such HF surgical instrument by simplifying assembly thereof. It is a further/another objective to realize an electric connection of individual components of the HF surgical instrument which can be provided at low cost.

This object is achieved by a HF surgical instrument comprising the features described herein and by a method of assembling a HF surgical instrument comprising the features described herein.

According to a first independent aspect of the invention, a HF surgical instrument includes two instrument branches movable toward each other into a closing position each of which is equipped with at least one electrode. The electrodes can be supplied with electric power by means of a power source. In accordance with the invention, the HF surgical instrument comprises a separately configured bridging means which may especially be a printed board which can preferably be machine-equipped. The bridging means can be connected to the power source via at least one terminal or at least one line and includes at least one electrically conductive contact point for supplying electric power to the at least one electrode. The bridging means formed separately from the HF surgical instrument and/or from the electrode can be introduced to the at least one of the two instrument branches so that the at least one electrically conductive contact point electrically contacts the at least one electrode and, resp., can be made to contact the same.

In other words, the HF surgical instrument according to the invention comprises a bridging means formed separately from the electrode by means of which bridging means an electric line guided to the HF surgical instrument and, resp., ending into the same can be connected to an electric contact point of an electrode in an electrically conductive manner. At least the electric connection between the bridging means and the contact point of the electrode may be a non-cohesive connection. In this context, a non-cohesive electric connection is understood to be any type of electrically conductive connection in which the respective connecting partners are not held together by atomic or molecular forces acting therebetween. That is to say, the bridging means formed and, resp., manufactured in a non-cohesive manner does not include any soldering, welding or gluing connection or similar type of connection at least between itself and the contact point of the at least one electrode of the handle unit. In particular, this connection which according to the invention is formed to be non-cohesive, in contrast to a soldered connection, is a connection releasable in a non-destructive manner. The non-cohesive connection between the bridging means and the plurality of segmented electrodes offers the advantage that a plurality of individual soldered connections between the electric line and the plurality of segmented electrodes may be saved. Compared to the solution suggested in the state of the art, where a sheet metal is arranged on each of the plurality of electrodes, in this case the assembling expenditure can be significantly reduced.

In this context, a bridging means is understood to be a means, adapter or component which is electrically conductive at least in portions and by which a spatial distance between the electric line guided to the HF surgical instrument and guided into a housing thereof, respectively, and the at least one electrode to be supplied with electric power can be overcome or bridged. That is to say, the bridging means according to the invention is configured to effect or bring about a spatial connection between the electric line and the at least one electrode of the HF surgical instrument.

The electric line guided to the surgical instrument and ending into a housing of the surgical instrument or the handle unit, respectively, may be arranged to electrically conduct electric power from an external power source, preferably from a HF generator, to the HF surgical instrument and to the at least one electrode, respectively. The electric line may be a multi-core line and may be adapted to the respective mains of the respective region of use for electric connection to the HF generator and via the same.

The bridging means formed separately or, resp., as a component separate from the at least one electrode and/or from the handle unit and adapted to be (separately) introduced to the HF surgical instrument advantageously enables the bridging means to be fabricated separately from the remaining components of the HF surgical instruments or else to be pre-fabricated or pre-mounted, respectively. Thus, for final assembly of the HF surgical instrument, the bridging means can be introduced and, resp., inserted into the same and fastened thereto, if necessary.

That is to say that no soldered connection has to be established between the at least one electrode and the electric line, which under certain circumstances, for example for reasons of operational safety, would be difficult in a clean room. In addition, by dispensing with a manually manufactured soldered connection the expenditure of work and time can be significantly reduced, thus causing also the manufacturing costs for a HF surgical instrument to be reduced. Moreover, by the use of a machine-equipped printed board a comparatively high reproducibility in manufacturing the printed board and thus in assembling the HF surgical instrument can be achieved. Especially compared to a manually fabricated soldered connection, in this way higher product safety and product quality can be obtained, wherein depending on the piece items to be fabricated additionally the manufacturing costs can be reduced.

The assembly is facilitated and enabled at all with a plurality of electrodes by the wireless connection between the electric line and the electrode to be supplied with electric power. Furthermore, also the handling and, resp., the mobility of the instrument branch can be improved, as no or at least comparatively few electric lines (cables) have to be guided through the instrument branch. For example, the HF surgical instrument may also include a plurality of segmented or, resp., segmental electrodes all of which are non-cohesively connectable to the electric line by the bridging means. That is to say that the handle member of the HF surgical instrument may also have plural segmentally arranged electrodes which are connectable to the electric line via the bridging means in a non-cohesive manner. The non-cohesive connection between the bridging means and the plurality of segmented electrodes offers the advantage that a plurality of individual soldered connections between the electric line and the plurality of segmented electrodes can be saved. Compared to the solution suggested in prior art in which a sheet metal is arranged on each of the plurality of electrodes, the assembling effort can be significantly reduced in this case.

In addition, the invention advantageously causes a comparatively small error rate to occur with the electric pairing of the electric line and the electrode. Moreover, by the connection releasable from the HF surgical device also the maintenance thereof is improved as the bridging means can be exchanged without any important effort. Furthermore, also electrodes which are difficult to reach can be easily supplied with electric power.

Since the degree of automation can be enormously increased by means of the interconnected printed board and, resp., the bridging means, the production can be more economic, which is of great importance especially with single-use instruments.

It has turned out to be especially expedient when the at least one electrically conductive contact point of the bridging means and/or the electrode includes an electrically conducting spring contact element which causes an electrically conductive pressure contact between the contact point and the electrode. In this way manufacturing tolerances can be compensated which may occur, for example, on a housing of the HF surgical instrument, on the bridging means or the electrode. Moreover, such pressure contact permits an especially reliable electrically conducting connection between the electrode and an electric power source. Such pressure contact enables especially simple assembly of the HF surgical instrument.

Another, possibly independent or additional aspect of the invention provides that the bridging means, when it is introduced loosely to the instrument branch, is fixed by force closure in the instrument branch via the pressure contact between the at least one spring contact and the at least one electrode. The pressure contact can be configured, for example, so that the bridging means can be clamped in the HF surgical instrument, especially between the electrode and a housing portion of the HF surgical instrument. Such configuration of the bridging means and, resp., the pressure contact imparts to the spring contact element of the bridging means a double function which enables an electrically conducting connection and, at the same time, a non-positive fixation of the bridging means in the HF surgical instrument, for instance within a housing portion thereof. Said non-positive fixation additionally allows the bridging means to be assembled without using any additional tool. Also non-destructive dismounting of the bridging means without the use of a tool is enabled in this way.

In accordance with an advantageous development of the invention, the at least one spring contact element can produce a releasable locking engagement between the instrument branch and the bridging means in a provided contact position. For this purpose, for example a recess in a housing portion of the HF surgical instrument may be formed into which the bridging means can be inserted. In this way, a non-positive and positive fixation of the bridging means can be obtained in the HF surgical instrument without the use of a tool.

It has turned out to be especially advantageous when the bridging means can be inserted via an axial aperture on the distal side of the instrument branch in the axial direction into the instrument branch. This allows an especially simple structure of the instrument branch.

According to an aspect of the invention, the bridging means can be inserted from the outside of the instrument branch, e.g. from the lower side of the lower instrument branch, into the instrument branch or the electrode holding fixture, respectively, so that the at least one contact point enters into contact with the at least one electrode and electrically contacts the same. The bridging means may be fixed on the instrument branch and, resp., the electrode holding fixture in different ways, for example by form closure, by means of pins or screws.

Another, possibly independent or additional aspect of the invention provides that the at least one electrically conductive terminal of the bridging means includes a clamping-cutting element for a cutting and/or clamping electric connection to an electric line connected to the electric power source. Alternatively, this connection can be brought about by crimping. In this way, also for the electrically conductive connection between the electric power source and, resp., the electric line and the bridging means a (cohesive) soldered connection can be dispensed with. Thus the strands of the electric line and the clamping-cutting elements or contacts can be interconnected even in the clean room. In this case, neither at the interface to the electric supply line nor at the interface to the at least one electrode a cohesive connection is provided, which facilitates or even enables the assembly. In other words, all contacts and terminals are solderless.

As an alternative hereto, the at least one electrically conductive terminal may be formed by a soldering eyelet for cohesive electric connection to an electric line connected to the power source. Thus a comparatively safe electrically conductive contact can be ensured between the electric power source and the bridging means. In addition, the soldering eyelet permits a soldered connection which is comparatively easy to manufacture at a relatively easily accessible position of the bridging means. Advantageously, the soldering eyelet may be arranged on the bridging means so that a wireless electric contacting is possible in the entire end portion of the HF surgical instrument.

Another, possibly independent or additional aspect of the invention provides that one of the two instrument branches is directly connected to the power source via a line and the other of the two instrument branches is indirectly supplied with electric power via the one instrument branch. At the bridging means of the one instrument branch a first contact, preferably a spring contact, and at the bridging means of the other instrument branch a second contact, preferably a spring contact, may be provided which enter into electrically conductive contact at least in the closing position of the two instrument branches. In this way it is advantageously possible to dispense with a separate power supply for the other instrument branch, thus permitting simple and synchronous current supply to the electrodes of both instrument branches. This has turned out to be advantageous also for safety reasons, as current is supplied to the opposed electrodes in the closing position only, i.e. when the interacting contacts are actuated by mutual contact. Moreover, the mobility of the two instrument branches, especially the mobility of the instrument branch supplied with electric power indirectly via the one instrument branch, is enormously improved as the former instrument branch is not controlled at all by a (separate) electric line.

The invention also relates to a method of assembling an HF surgical instrument including two instrument branches movable toward each other into a closing position, each of which can be equipped with at least one electrode and can be supplied with electric power from a power source. In accordance with the invention, the method comprises the following steps of:

equipping each instrument branch with at least one electrode;

connecting a bridging means formed separately at least from the electrode, especially a printed board preferably adapted to be machine-equipped, via at least one electric connection or at least one electric line to the power source;

inserting the bridging means which has at least one contact point for supplying electric power to the at least one electrode into at least one instrument branch; and contacting the at least one contact point of the bridging means with the at least one electrode.

By the use of said (assembly) method an HF surgical instrument which excels by an especially advantageously simple manufacturing and handling can be assembled and provided, respectively.

BRIEF DESCRIPTION OF THE DRAWING FIGURES

Figure 2:
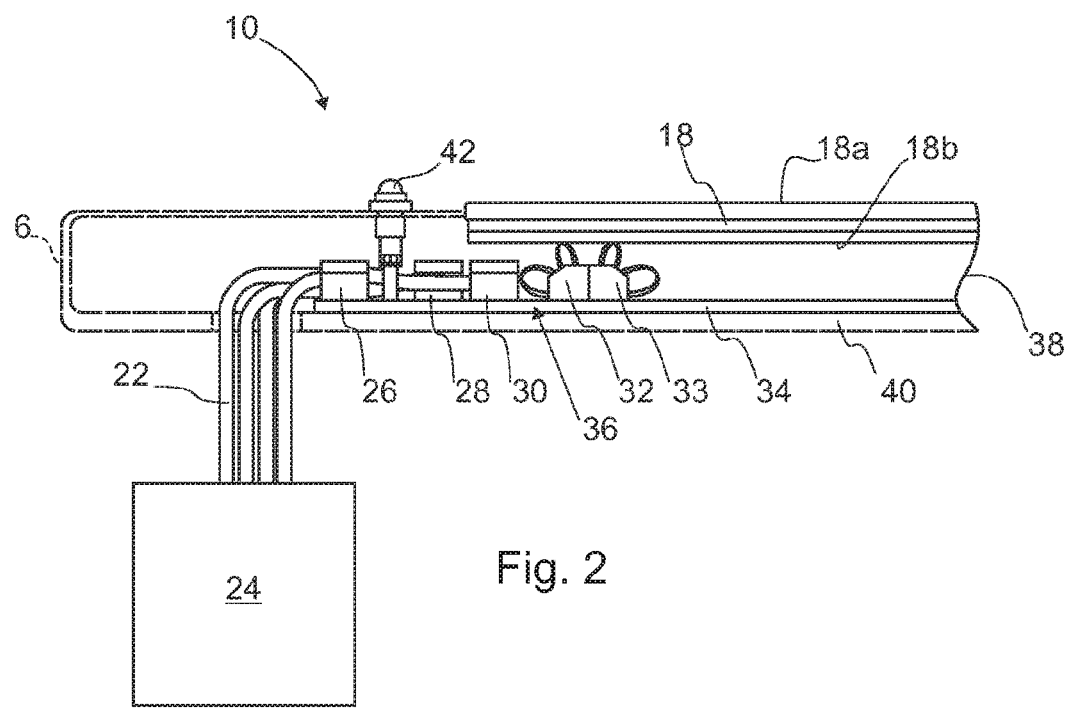
Figure 3:
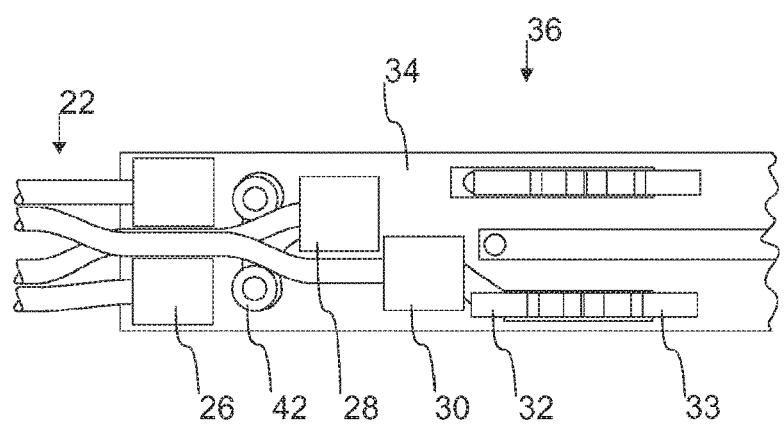
Figure 4:
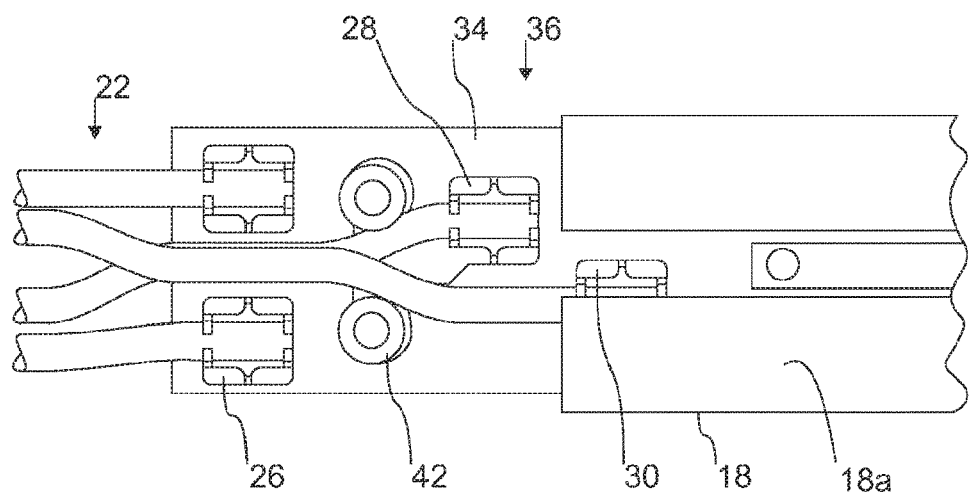
Figure 5:
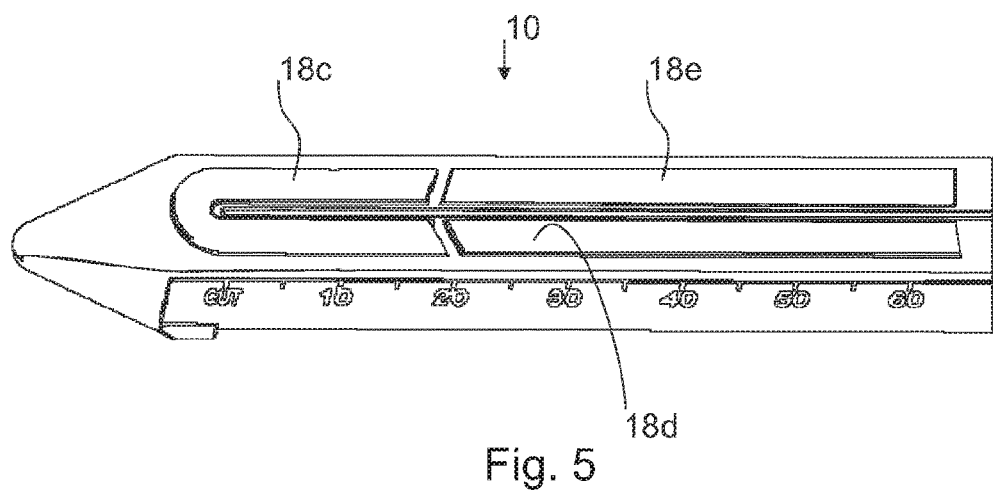

Hereinafter the invention will be illustrated in detail by way of a preferred embodiment with reference to the accompanying figures, in which:

FIG. 1 shows a perspective side view of a HF surgical instrument according to the invention which is connected to an external electric power source, FIG. 2 shows a sectional view across a HF surgical instrument according to the invention, especially a section across a handle unit and, resp., an instrument branch of the HF surgical instrument, FIG. 3 shows a top view onto a partly freely cut bridging means of a HF surgical instrument according to the invention, FIG. 4 shows a top view onto a partly freely cut bridging means of a HF surgical instrument according to the invention in which, for the purpose of illustration, individual components are not shown, and FIG. 5 shows a perspective side view of an instrument branch including segmented electrodes of a HF surgical instrument according to the invention.

DETAILED DESCRIPTION

Equal or similar components are provided throughout with equal reference numerals.

FIG. 1 illustrates an embodiment of a HF surgical instrument 1 according to the invention in the form of a bipolar-type HF sealing instrument in a perspective side view. Said HF surgical instrument 1 enables a user to bring about a thermally induced modification or destruction of tissue cells. For example, vessels and tissue structures of a human body can be permanently and safely thermo-fused by the HF surgical instrument 1.

The HF surgical instrument 1 shown in FIG. 1 includes two instrument halves 2, 4 which are separably hinge-like connected (connectable), each consisting of a respective handle unit 6, 8 comprising a respective instrument branch 10, 12 arranged in the longitudinal instrument direction (viewed by the user) distally hereto. It is evident from FIG. 1 that the instrument branches 10 and 12 are opposed to each other so as to clamp the tissue to be treated (not shown) therebetween. Each of the lower handle unit 6 in FIG. 1 and the upper handle unit 8 in FIG. 1 has a handle shell 14, 16 ergonomically shaped for a user which are fabricated, for example, of plastic or sheet material suited for medical application.

The lower instrument branch 10 includes on a side facing the other upper instrument branch 12 an electrode 18 operable with electric power which is evident in outlines only in FIG. 1. The upper instrument branch 12 includes equally on a side facing the other lower instrument branch 10 a further electrode 20 which is also evident in outlines only in FIG. 1. For supplying electric power to the HF surgical instrument 1 the latter and, resp., one of the handle units 6 of 8 includes a housing aperture not denoted in detail through which an electric line 22 is guided to the or into the HF surgical instrument 1. The electric line 22 is electrically connected to an external electric power source 24 which in this embodiment is a HF generator for generating high-frequency alternating current (HF current). The supply of the two electrodes 18, 20 with electric power from the electric power source 24 is described in detail further below.

FIG. 2 illustrates a sectional view across the HF surgical instrument 1, especially a section across the lower handle unit 6 and, resp., the lower instrument branch 10 of the HF surgical instrument 1. It is evident that the electrode 18 is incorporated in the instrument branch 10 and has an active surface 18a exposed to the outside which is arranged to contact the tissue to be treated. It is further evident that the electric line 22 is guided from the electric power source 24 into the HF surgical instrument 1 and ends into three contact elements 26, 28, 30 which in this embodiment are a cutting and/or clamping element for cutting and/or clamping electrically conductive fastening of the line 22. By this type of contact elements 26, 28, 30 it is possible in each case to insert the electric line 22, possibly without prior removal of its insulation surrounding the electric conductor, directly into the respective contact element 26, 28 or 30 and to fasten it thereto. Each of the three contact elements 26, 28 and 30 includes a cutting member which cuts through the insulation of the electric line 22, if necessary, and in this way establishes an electric connection between itself and the individual electricity-conducting cores of the electric line 22. Moreover, the contact elements 26, 28, 30 comprise a clamping member by the clamping engagement of which the electric line is fastened by clamping to the contact elements 26, 28, 30.

It can further be inferred from FIG. 2 that the contact elements 26, 28, 30 in the form of a cutting and/or clamping element are in contact, i.e. adjacent to spring contact elements 32, 33, which are arranged distally next to the contact element 30 in FIG. 2. In particular, there is an electric connection between the contact element 30 to which the electric line 22 is fastened and the spring contact element 32 by direct contact of said two component parts. In this way the electric power generated by the electric power source 24 can be guided via the electric line 22 and the contact element 30 to the spring contact element 32. It is further evident from FIG. 2 that a spring member of the spring contact element 32 is arranged inside the handle unit 6 so that it is pressed from below against a lower surface side 18b of the electrode 18. In this manner the spring contact element 32 is in electrically conducting contact with the side 18b of the electrode 18 facing the active surface 18a so as to supply the electric power generated by the electric power source 24 via the electric line 22, the contact element 30 and the spring contact element 32 to the electrode 18.

FIG. 2 also illustrates that the elements used for transmitting the electric power in this embodiment, viz. the contact elements 26, 28, 30 and the spring contact element 32, are arranged on a joint side of a printed board 34. The printed board 34 and the elements 26, 28, 30 and 32 arranged and, resp., fastened thereon in this manner jointly constitute a bridging means 36 which bridges and, resp., overcomes the spatial distance between the electric line 22 ending into the HF-surgical instrument 1 and the electrode 18 to be supplied with current so as to establish an electric connection between said two components in this way.

The printed board 34 preferably is a pre-fabricated, equally preferably machine-fabricated component which during final assembly of the HF surgical instrument 1 is introduced or inserted into a distally arranged receiving opening 38 formed between the electrode 18 and a housing wall 40 belonging to the handle unit 6. The printed board 34 arranged between the electrode 18 and the housing wall 40 is clamped by the spring contact elements 32, 33 resting on the (tightly mounted) electrode 18 in the direction of the housing wall 40, thus causing the printed board 34 to be non-positively fixed inside the receiving opening so that no further fastening of the printed board 34 has to be provided. A further fastening possibility (not shown) may be provided as an option, however.

Moreover, in FIG. 2 a resiliently or, resp., floatingly supported contact element 42 is shown which is equally electrically connected to the electric line 22. The resiliently supported contact element 42 serves for establishing an electric connection to the other handle unit 8 or instrument branch 12 not shown in FIG. 2 and, respectively, to the electrode 20 arranged thereon by contacting the same. In this manner, an electric connection can be established between the electric line 22 and the electrode 20 via the printed board 34 and, resp., by the resiliently supported contact element 42 arranged thereon when the two handle units 6, 8 and the instrument branches 10, 12, respectively, are approaching each other. The resiliently supported contact element 42 is shown, for example, in FIG. 1 illustrating a perspective side view of the HF surgical instrument 1. The spring contact 42 includes a spring-biased contact pin or a spring tongue extending from one of the instrument halves 2 in the direction of the other instrument half 4 so as to be actuated by the same. The spring contact 42 does not contact a corresponding contact element on the other instrument branch 12 before the instrument branches 10, 12 are closed. The contact on the other instrument branch is electrically connected to the electrode 20 and to the electrode segments thereof, respectively. Hence only when or shortly before the predetermined closing force is reached, electric current is released from a power source, preferably an external HF generator to the two instrument branches 10, 12. In this way the electrode 20 of the other (upper) instrument branch 12 is controlled indirectly by the one (lower) instrument branch 10, more exactly speaking via the bridging means 36 provided in the same.

FIG. 3 illustrates a top view onto the partly freely cut bridging means 36 in the form of the printed board 34 of the HF surgical instrument 1. It is evident that the printed board 34 is equipped with the contact elements 26, 28, 30 and the resiliently supported contact element 42 such that the electric line 22 is easily connectable and, resp., may be connected to each of said elements.

From FIG. 4 illustrating a top view onto the partly freely cut bridging means in the form of the printed board 34 of the HF surgical instrument 1, in which for illustration purposes individual components are not shown, the functioning of the contact elements 26, 28, 30 configured as respective cutting and/or clamping elements can be taken. In particular, in FIG. 4 a respective upper cover (not otherwise specified) of the contact elements 26, 28, 30 configured as cutting and/or clamping elements is not represented so as to be able to clearly illustrate the insertion and clamping of individual cores (not otherwise specified) of the electric line 22 by means of the clamping member. It is further visible from FIG. 4 that the resiliently supported contact elements 42 are in electric connection with the contact element 30 so that the electrode 20 of the instrument branch 10 can be supplied with electric power.

In FIG. 5 illustrating a perspective side view of the instrument branch 10 including segmented or segmental electrodes 18c, 18d and 18e of the HF surgical instrument 1 it is evident that also plural separately arranged, viz. segmented, electrodes can be supplied with electric power by means of the bridging means in the form of the printed board 34. For this purpose, merely plural electrically conductive contact elements or spring contact elements are required to contact the individual segments of the electrode. In order to ensure sufficient contacting also two or more spring contact elements 32, 33 may be provided rather than one for an electrode 18 and, resp., an electrode segment 18c, 18d, 18e.

The assembly of the HF surgical instrument 1 can proceed as described hereinafter.

At first the HF surgical instrument 1 comprising the two instrument branches 10, 12 movable toward each other into a closing position is fabricated and provided in a way known per se. In particular, the instrument branches 10, 12 are equipped with the electrodes 18, 20.

Equipment of the one or lower instrument branch 18 and, resp., the electrode support can be carried out by injection molding in that the electrodes or electrode segments 18 are inserted into the injection molding tool and plastic material is injection-molded around the same.

In a working step independent thereof (in time) the bridging means 36, which in this embodiment is a machine-equipped printed board 34, is fabricated and provided. This separately configured bridging means 36 is connected to the electric line 22 by means of the contact elements 26, 28, 30 in that the current-conducting cores are inserted in the contact elements 26, 28, 30 and the latter are subsequently actuated while cutting and clamping the cores.

In order to establish an electrically conductive (pressure) contact between the spring contact elements 32, 33 and the electrode 18 the bridging means 36 is inserted in the receiving opening 38 orientated in such way that the spring contact elements 32, 33 are pressed by the spring part against the lower surface side 18b of the electrode 18 and thus are made to contact the same. In this context, the printed board 34 rests within the receiving opening 38 on the housing wall 40 by one side facing the side supporting the contact elements 26, 28, 30 and the spring contact elements 32, 33. The printed board 36 is introduced so that it is positively accommodated and secured in the instrument branch 10 in the axial direction. By this supporting arrangement of the printed board 34 the latter is held in the receiving opening 38 on the one hand by force closure and on the other hand by form closure and in electrically conductive contact with the lower surface side 18b of the electrode 18.

Instead of axially sliding the bridging means 36 into the instrument branch, it can alternatively be inserted into the instrument branch 10 open at the lower side and, resp., the electrode support so that the spring contact elements 32, 34 are pressed with the spring part against the lower surface side 18b of the electrode 18 and are thus made to contact the same. Subsequently, the bridging means 36 is fastened to the electrode support, e.g. by means of pins or screws. The lower side of the bridging means 36 and, resp., the printed board is designed to close the instrument branch 10 to be flush.

Starting from the shown embodiment, the invention may be modified in various respects. For example, it is imaginable that the electric line 22 and, resp., the individual cores thereof are fastened to be electrically conductive by means of one or more soldering eyelets (not shown), for example by soldering, rather than by means of the contact elements 26, 28, 30 configured as cutting and/or clamping elements, to the bridging means 36 and to the printed board 34, respectively.

There is disclosed a HF surgical instrument comprising two instrument branches movable toward each other into a closing position each of which is equipped with at least one electrode and is supplied with electric power from a power source. According to the invention, the HF surgical instrument comprises a separately formed bridging means, especially a printed board which is preferably adapted to be machine-equipped and which is connectable to the power source via at least one electric connection or at least one electric line and for supplying the at least one electrode with electric power includes at least one electrically conductive contact point which can be introduced to at least one of the two instrument branches so that the at least one contact point is electrically contacted by/made to contact the at least one electrode.

Furthermore, there is disclosed a method of mounting an HF surgical instrument including two instrument branches movable toward each other in a closing position each of which can be equipped with at least one electrode and can be supplied with electric power from a power source. In accordance with the invention, the method comprises the steps of: equipping the instrument branch with at least one respective electrode; connecting a separately configured bridging means, especially a printed board which can preferably be machine-equipped to the power source via at least one connector or at least one line; inserting the bridging means which includes at least one contact point for supplying the at least one electrode with electric power into at least one instrument branch; and making the at least one contact point of the bridging means to contact the at least one electrode.

The invention claimed is:

1. A HF surgical instrument comprising:
a first instrument branch and a second instrument branch that are movable toward each other into a closing position, the first instrument branch equipped with at least one first electrode, and the second instrument branch equipped with at least one second electrode, the first instrument branch and the second instrument branch each configured to be supplied with electric power from a power source; and
a separately configured bridge comprising a printed circuit board and connectable to the power source via at least one electric connection or at least one electric line, the bridge including a first contact point for supplying the at least one first electrode with electric power and a second contact point for supplying the at least one second electrode with electric power, the bridge configured to be introduced to the first instrument branch such that the first contact point electrically contacts the at least one first electrode,
the first instrument branch having a receiving opening beneath the at least one first electrode, the receiving opening formed between the at least one first electrode and a housing wall of a handle unit, the bridge being insertable into the receiving opening and advanceable between the housing wall and the at least one first electrode and into the first instrument branch in a longitudinal direction.

2. The HF surgical instrument according to claim 1, wherein the first contact point or the at least one first electrode has at least one electrically conductive spring contact element which causes an electrically conductive pressure contact between the first contact point and the at least one first electrode.

3. The HF surgical instrument according to claim 2, wherein the bridge is introduced into the first instrument branch and non-positively fixed in the first instrument branch via the electrically conductive pressure contact between the first contact point and the at least one first electrode.

4. The HF surgical instrument according to claim 2, wherein the at least one electrically conductive spring contact element produces a releasable locking engagement between the first instrument branch and the bridge in a provided contact position.

5. The HF surgical instrument according to claim 1, wherein the at least one electric connection or at least one electric line comprises a clamping-cutting element for clamping electric connection to the power source.

6. The HF surgical instrument according to claim 1, wherein the at least one electric connection or at least one electric line is formed by a soldering eyelet for cohesive electric connection to the power source.

7. The HF surgical instrument according to claim 1, wherein one of the first instrument branch and the second instrument branch is directly connected to the power source and the other of the first instrument branch and the second instrument branch is supplied with electric power indirectly via said one of the first instrument branch and the second instrument branch, and wherein, at the bridge, the second contact point electrically contacts a corresponding contact at said other of the first instrument branch and the second instrument branch at least in the closing position of the first instrument branch and the second instrument branch.

8. A HF surgical instrument comprising:
a first instrument branch and a second instrument branch that are movable toward each other into a closing position, the first instrument branch being equipped with at least one first electrode and the second instrument branch being equipped with at least one second electrode, the first instrument branch and the second instrument branch each configured to be supplied with electric power from a power source; and
a separately configured bridge comprising a printed circuit board and connectable to the power source via at least one electric connection or at least one electric line, the bridge including a first spring-biased contact point for supplying the at least one first electrode with electric power by spring contact, the bridge also including a second spring-biased contact point for supplying the at least one second electrode with electric power by spring contact, the bridge configured to be introduced to at least one of the first instrument branch and the second instrument branch such that at least one of the first and second spring contact points electrically contacts at least one of the first and second electrodes.

9. The HF surgical instrument according to claim 8, wherein the first spring-biased contact point has a first electrically conductive spring contact element which causes an electrically conductive pressure contact between the first spring-biased contact point and the at least one first electrode.

10. The HF surgical instrument according to claim 9, wherein the second spring-biased contact point has a second electrically conductive spring contact element which causes an electrically conductive pressure contact between the second spring-biased contact point and the at least one second electrode.

11. The HF surgical instrument according to claim 9, wherein the bridge is introduced into the first instrument branch and non-positively fixed in the first instrument branch via the electrically conductive pressure contact between the first spring-biased contact point and the at least one first electrode.

12. The HF surgical instrument according to claim 9, wherein the first electrically conductive spring contact element produces a releasable locking engagement between the first instrument branch and the bridge in a provided contact position.

13. The HF surgical instrument according to claim 8, wherein the at least one electric connection or at least one electric line comprises a clamping-cutting element for clamping electric connection to the power source.

14. The HF surgical instrument according to claim 8, wherein the at least one electric connection or at least one electric line is formed by a soldering eyelet for cohesive electric connection to the power source.

15. The HF surgical instrument according to claim 8, wherein the first instrument branch is directly connected to the power source and the second instrument branch is supplied with electric power indirectly via the first instrument branch, and wherein, at the bridge, the second spring-biased contact point electrically contacts a corresponding contact at said second instrument branch at least in the closing position of the first instrument branch and the second instrument branch.

\* \* \* \* \*